US011352335B2

(12) United States Patent
Zell et al.

(10) Patent No.: US 11,352,335 B2
(45) Date of Patent: Jun. 7, 2022

(54) SYNTHESIS OF 5-CHLORO-2-[(3,4,4-TRIFLUORO-3-BUTEN-1-YL)THIO]-THIAZOLE

(71) Applicant: Adama Makhteshim, Ltd., Beer Sheva (IL)

(72) Inventors: Thomas Zell, Beer Sheva (IL); Boris Rubinov, Beer Sheva (IL)

(73) Assignee: ADAMA MAKHTESHIM, LTD., Beer Sheva (IL)

( * ) Notice: Subject to any disclaimer, the term of this patent is extended or adjusted under 35 U.S.C. 154(b) by 0 days.

(21) Appl. No.: 16/964,047

(22) PCT Filed: Jan. 22, 2019

(86) PCT No.: PCT/IB2019/050533
§ 371 (c)(1),
(2) Date: Jul. 22, 2020

(87) PCT Pub. No.: WO2019/145857
PCT Pub. Date: Aug. 1, 2019

(65) Prior Publication Data
US 2021/0070719 A1 Mar. 11, 2021

Related U.S. Application Data

(60) Provisional application No. 62/620,769, filed on Jan. 23, 2018.

(51) Int. Cl.
*C07D 277/36* (2006.01)

(52) U.S. Cl.
CPC .................................. *C07D 277/36* (2013.01)

(58) Field of Classification Search
CPC .................................................... C07D 277/36
See application file for complete search history.

(56) References Cited

U.S. PATENT DOCUMENTS

| | | | |
|---|---|---|---|
| 5,085,698 A | 2/1992 | Ma et al. | |
| 5,708,095 A | 1/1998 | Grezzo Page et al. | |
| 6,153,705 A | 11/2000 | Corpart et al. | |
| 6,734,198 B1 | 5/2004 | Watanabe et al. | |
| 6,743,814 B2 | 6/2004 | Corpart et al. | |
| 6,777,513 B1 | 8/2004 | Destarac et al. | |
| 6,787,654 B2 | 9/2004 | Krich et al. | |
| 8,013,167 B1 | 9/2011 | O'Sullivan et al. | |
| 2002/0151648 A1 | 10/2002 | Fasano et al. | |
| 2007/0155680 A1 | 7/2007 | Andersch et al. | |
| 2011/0039704 A1 | 2/2011 | Sixl et al. | |
| 2011/0224076 A1 | 9/2011 | Sowa | |
| 2011/0311503 A1 | 12/2011 | Christian et al. | |
| 2013/0085281 A1 | 4/2013 | Haight et al. | |
| 2014/0141977 A1 | 5/2014 | Wacket et al. | |
| 2015/0112063 A1 | 4/2015 | Pawar et al. | |
| 2021/0070719 A1 | 3/2021 | Zell et al. | |

FOREIGN PATENT DOCUMENTS

| | | |
|---|---|---|
| CN | 1359379 A | 7/2002 |
| CN | 104982431 A | 10/2015 |
| EP | 0 007 731 A2 | 2/1980 |
| WO | WO 1996/30421 A1 | 10/1996 |
| WO | WO 1997/046657 | 5/1997 |
| WO | WO 1998/01478 A1 | 1/1998 |
| WO | WO 1999/03894 A1 | 1/1998 |
| WO | WO 1998/58974 A1 | 12/1998 |
| WO | WO 1999/31144 A1 | 6/1999 |
| WO | WO 1999/35177 A1 | 7/1999 |
| WO | WO 1999/35178 A1 | 7/1999 |
| WO | WO 2000/020520 A1 | 4/2000 |
| WO | WO 2000/026308 A1 | 5/2000 |
| WO | WO 2000/75207 A1 | 12/2000 |
| WO | WO 2001/002378 A1 | 1/2001 |
| WO | WO 2001/066529 A1 | 9/2001 |
| WO | WO 2002/006259 A1 | 1/2002 |
| WO | WO 2002/10223 A2 | 2/2002 |
| WO | WO 2002/22688 A2 | 3/2002 |
| WO | WO 2002/26836 A2 | 4/2002 |
| WO | WO 2002/070861 A1 | 9/2002 |
| WO | WO 2004/095929 A1 | 11/2004 |

(Continued)

OTHER PUBLICATIONS

Mahajan, et al., "Efficient and Facile Chlorination of Industrially-Important Aromatic Compounds using NaCl/p-TsOH/NCS in Aqueous Media", Ind Eng Chem Res, Feb. 10, 2012, vol. 51, No. 10, pp. 3881-3886.
International Search Report dated Jul. 24, 2019 in connection with PCT International Application No. PCT/IB2019/050533.
Written Opinion (form PCT/ISA/237) dated Jul. 24, 2019 in connection with PCT International Application No. PCT/IB2019/050533.
International Search Report dated Jan. 14, 2004 in connection with PCT International Application No. PCT/EP2003/006511.
International Search Report dated Mar. 24, 2016 in connection with PCT International Application No. PCT/IL2015/050943.
International Search Report dated Jul. 6, 2017 in connection with PCT International Application No. PCT/IB2016/001863.
International Search Report dated Sep. 5, 2018 in connection with PCT International Application No. PCT/IB2018/000701.
International Search Report dated Nov. 5, 2019 in connection with PCT International Application No. PCT/IB2019/054929.

(Continued)

*Primary Examiner* — Shawquia Jackson
(74) *Attorney, Agent, or Firm* — Gary J. Gershik

(57) ABSTRACT

The present invention provides an improved process for preparing 5-chloro-2-[(3,4,4-trifluoro-3-buten-1-yl)thio]-thiazole comprising reacting 2-[(3,4,4-trifluoro-3-buten-1-yl)thio]-thiazole with N-chlorosuccinimide (NCS) in the presence of water, the improvement comprising performing the step of reacting the compound of formula (II) with NCS in the presence of a reduced amount of water. The present invention provides an improved process for preparing 5-chloro-2-[(3, 4,4-trifluoro-3-buten-1-yl)thio]-thiazole comprising reacting 2-[(3, 4,4-trifluoro-3-buten-1-yl)thio]-thiazole with N-chlorosuccinimide (NCS) in the presence of water, the improvement comprising performing the step of reacting the compound of formula (II) with an excess molar amount of NCS.

20 Claims, No Drawings

(56) References Cited

FOREIGN PATENT DOCUMENTS

| WO | WO 2004/095930 A1 | 11/2004 |
|---|---|---|
| WO | WO 2006/108553 A1 | 10/2006 |
| WO | WO 2007/081965 A2 | 7/2007 |
| WO | WO 2008/076807 A3 | 6/2008 |
| WO | WO 2010/035118 A1 | 4/2010 |
| WO | WO 2012/123094 A2 | 9/2012 |
| WO | WO 2013/004704 A1 | 1/2013 |
| WO | WO 2013/093578 A1 | 6/2013 |
| WO | WO 2013/107795 A2 | 7/2013 |
| WO | WO 2013/133706 A1 | 9/2013 |
| WO | WO 2013/186695 A1 | 12/2013 |
| WO | WO 2013/189776 A1 | 12/2013 |
| WO | WO 2015/049378 A1 | 4/2015 |
| WO | WO 2015/116716 A1 | 8/2015 |
| WO | WO 2007/098325 A1 | 6/2017 |

OTHER PUBLICATIONS

Written Opinion of the International Searching Authority dated Mar. 24, 2016 in connection with PCT International Application No. PCT/IL2015/050943.
Written Opinion of the International Searching Authority dated Jul. 6, 2017 in connection with PCT International Application No. PCT/IB2016/001863.
Written Opinion of the International Searching Authority dated Dec. 20, 2018 in connection with PCT International Application No. PCT/IB2018/000701.
Written Opinion of the International Searching Authority dated Dec. 19, 2019 in connection with PCT International Application No. PCT/IB2019/054929.
International Preliminary report on Patentability dated Jan. 3, 2005 in connection with PCT International Application No. PCT/EP2003/006511.
International Preliminary report on Patentability dated Mar. 21, 2017 in connection with PCT International Application No. PCT/IL2015/050943.
International Preliminary report on Patentability dated Jun. 12, 2018 in connection with PCT International Application No. PCT/IB2016/001863.
International Preliminary report on Patentability dated Jun. 11, 2019 in connection with PCT International Application No. PCT/IB2017/001636.
International Preliminary report on Patentability dated Dec. 10, 2019 in connection with PCT International Application No. PCT/IB2018/000701.
International Preliminary report on Patentability dated Jul. 28, 2020 in connection with PCT International Application No. PCT/IB2019/050533.
International Preliminary report on Patentability dated Dec. 15, 2020 in connection with PCT International Application No. PCT/IB2019/054929.
Office Action dated Mar. 3, 2021 in connection with Chinese Application No. 2017800759733 (with English translation).
Braun, D., "Initiation of Free Radical Polymerizaion by Thermal Cleavage of Carbon-Carbon Bonds", *Macromol. Symp.*, 1996, vol. 111, pp. 63-71.
Kennedy, R.J. and Stock A.M., "The Oxidation of Organic Substances by Potassium Peroxymonosulfate", *The Journal of Organic Chemistry*, 1960, vol. 25, No. 11, pp. 1901-1906.
Li, G. et al. "Fluoroalkane thioheterocyclic derivatives and their antitumor activity", *European Journal of Medicinal Chemistry*, 2015, vol. 93, pp. 423-430.
Liu, Y. et al., "Stabilized Polymeric Nanoparticles for Controlled and Efficient Release of Bifenthrin", *Pest Management Science*, 2008, vol. 64, No. 8, pp. 808-812.
Matyjaszewski, K. et al., "Controlled radical polymerizations: the use of alkyl iodides in degenerative transfer." *Macromolecules*, 1995, vol. 28, No. 6, pp. 2093-2095.
Otsu, T. and Yoshida, M., "Role of initiator-transfer agent-terminator (iniferter) in radical polymerizations: Polymer design by organic disulfides as iniferters", Makromol. Chern., Rapid Commun., 1982, vol. 3, pp. 127-132.
Rikkou-Kalourkoti, M. et al., "Group Transfer Polymerization", *Encyclopedia of Polymer Science and Technology*, 2013, vol. 99, pp. 1-17.
Spinelli (1998) Polymeric Dispersants in Ink Jet Technology, *Advanced Materials*, 1998, vol. 10, No. 15, pp. 1215-1218.
Wayland, B.B. et al., "Living Radical Polymerization of Acrylates by Organocobalt Porphyrin Complexes", *J. Am. Chem. Soc.*, 1994, vol. 116, pp. 7943-7944.
X3503: Technical Bulletin JEFFSPERSE X3503 Dispersant, HUNTSMAN, published Apr. 1, 2010 (retrieved from https://www.huntsmanservice.com/performance_products/Media%20Library/global/files/technical_bulletin_jeffsperse_x3503_0410.pdf).
STN Report 318290-96-9, Jan. 30, 2001.

SYNTHESIS OF 5-CHLORO-2-[(3,4,4-TRIFLUORO-3-BUTEN-1-YL)THIO]-THIAZOLE

CROSS-REFERENCE TO RELATED APPLICATIONS

This application is a § 371 national stage of PCT International Application No. PCT/IB2019/050533, filed Jan. 22, 2019, claiming the benefit of U.S. Provisional Patent Application No. 62/620,769, filed Jan. 23, 2018, the contents of which is hereby incorporated by reference into the application.

Throughout this application various publications are referenced. The disclosures of these documents in their entireties are hereby incorporated by reference into this application in order to more fully describe the state of the art to which this invention pertains.

TECHNICAL FIELD

The present subject matter relates to an efficient procedure for preparing 5-chloro-2-[(3,4, 4-trifluoro-3-buten-1-yl)thio]-thiazole.

BACKGROUND OF THE INVENTION

Fluensulfone (5-chloro-2-(3,4,4-trifluorobut-3-enylsulfonyl)-1,3-thiazole; CAS No. 318290-98-1) is a very efficient active ingredient highly powerful against plant-parasitic nematodes. Fluensulfone is a heterocyclic fluoroalkenyl sulfone nematicide which has a significantly reduced environmental impact with low toxicity to non-target insects and mammals. Fluensulfone's mode of action is distinct from currently available nematicides and therefore presents a promising entity for crop protection although the precise mode of action of fluensulfone is currently unknown.

5-chloro-2-[(3,4,4-trifluoro-3-buten-1-yl)thio]-thiazole, compound (I), is an important intermediate in the preparation of fluensulfone

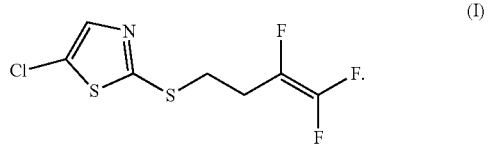 [SMILES: FC(F)=C(F)CCSc1ncc(Cl)s1]

(I)

Compound (I) is prepared through a chlorination reaction of the compound of formula (II)

(II)

Several chlorinating agents are known in the art such as chlorine gas, sulfuryl chloride and N-chlorosuccinimide (NCS).

Each of the procedures currently known in the art has disadvantages and cannot be used in an efficient manner for the chlorination of the compound of formula (II). Such disadvantages are, for example, lack of selectivity and formation of impurities and over-chlorinated by-products such as compound [295] and compound [329].

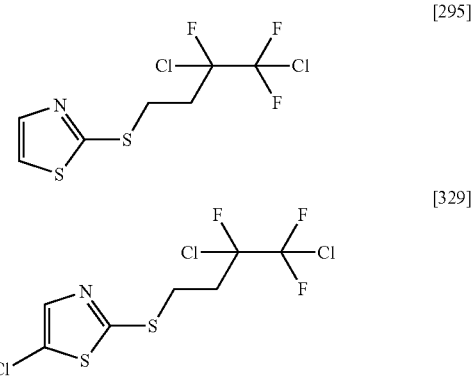

An additional problem associated with chlorine gas and sulfuryl chloride is corrosion, which makes the production of large scale very difficult.

European Journal of Medicinal Chemistry (2015), 93, 423-430, discloses a chlorination process with NCS in carbon tetrachloride, which is a non-polar solvent. In this process, the chlorinated product is obtained together with the corresponding di-chlorinated and the tri-chlorinated by-products.

U.S. Pat. Nos. 6,734,198 and 6,743,814 disclose trifluorobutene compounds, and preparation thereof using, inter alia, NCS in the presence of a polar or a non-polar solvent.

The processes disclosed in the art are performed under harsh reaction conditions and generates low yields. Thus, there is a need for an economical, universal, and efficient process for preparing compound (I) in high selectivity, yield, conversion and purity.

There is also a need for a selective process for obtaining compound (I). It would be advantageous to have a highly selective process with molar equivalent amount of chlorinating agent.

SUMMARY OF THE INVENTION

The present invention provides an improved process for preparing a compound of formula (I)

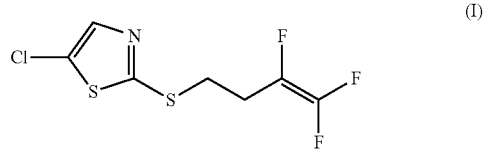

(I)

which comprises reacting a compound of formula (II)

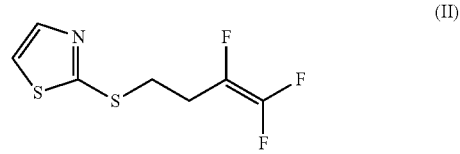 [SMILES: FC(F)=C(F)CCSc1nccs1]

(II)

with N-chlorosuccinimide (NCS) in the presence of water, the improvement comprising performing the step of reacting the compound of formula (II) with NCS in the presence of a reduced amount of water.

The present invention also provides an improved process for preparing a compound of formula (I)

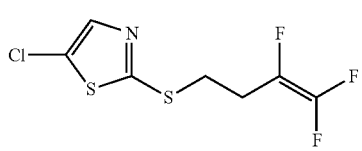

which comprises reacting a compound of formula (II)

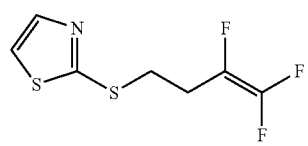

with N-chlorosuccinimide (NCS) in the presence of water, the improvement comprising performing the step of reacting the compound of formula (II) with an excess molar amount of NCS.

The present invention also provides a process of preparing a compound of formula (I)

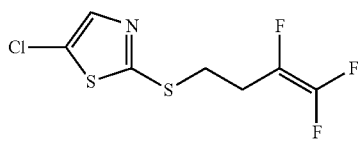

comprising reacting a compound of formula (II)

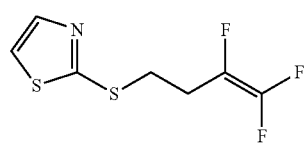

with N-chlorosuccinimide (NCS) in a low water content reaction mixture, wherein the process comprises (i) obtaining a low water content batch of the compound of formula (II), and/or (ii) obtaining a low water content batch of NCS.

The present invention also provides a compound of formula (I)

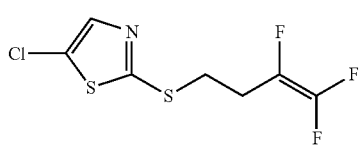

prepared using any one of the processes or methods disclosed herein.

The present invention also provides a method of increasing yield of a compound of formula (I) in a process of synthesizing the compound of formula (I) which involves reacting a compound of formula (II) with NCS in the presence of water, wherein the method comprises performing the step of reacting the compound of formula (II) with NCS in the presence of less water so as to increase the yield of the compound of formula (I) relative to a process where more water is present during the reaction step.

The present invention also provides a method of increasing yield of a compound of formula (I) in a process of synthesizing the compound of formula (I) which involves reacting a compound of formula (II) with NCS in the presence of water, wherein the method comprises adding excess molar amount of NCS to the reaction mixture.

The present invention also provides a process for preparing fluensulfone having the structure (III)

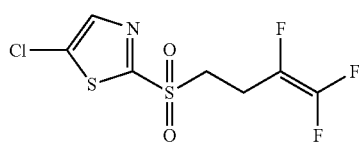

comprising converting the compound of formula (I) prepared according to any one of the processes disclosed herein.

The present invention also provides a compound of formula (III)

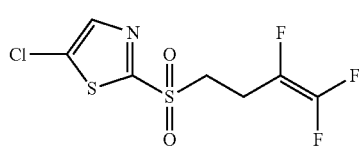

prepared using any one of the processes disclosed herein.

DETAILED DESCRIPTION OF THE INVENTION

Definitions

Prior to setting forth the present subject matter in detail, it may be helpful to provide definitions of certain terms to be used herein. Unless defined otherwise, all technical and scientific terms used herein have the same meaning as is commonly understood by one of skill in the art to which this subject matter pertains. The following definitions are provided for clarity.

The term "a" or "an" as used herein includes the singular and the plural, unless specifically stated otherwise. Therefore, the terms "a," "an," or "at least one" can be used interchangeably in this application.

As used herein, the term "about" when used in connection with a numerical value includes ±10% from the indicated value. In addition, all ranges directed to the same component or property herein are inclusive of the endpoints, are independently combinable, and include all intermediate points and ranges. It is understood that where a parameter range is provided, all integers within that range, and tenths thereof, are also provided by the invention.

As used herein, the term "mixture" or "combination" refers, but is not limited to, a combination in any physical form, e.g., blend, solution, alloy, or the like.

As used herein, the term "substantially free of water" when used in connection with a reaction mixture means that the reaction mixture has a water content of less than or equal to about 5 wt. %.

As used herein, the term "low water content" when used in connection with a batch of the compound of formula (II) means that the batch of the compound of formula (II) has a concentration of water less than or equal to 0.2 wt. %.

As used herein, the term "low water content" when used in connection with a batch of the NCS means that the batch of NCS has a concentration of water less than or equal to 2 wt. %.

As used herein, the term "low water content" when used in connection with a solvent means that the solvent has a concentration of water sufficiently low such that the reaction mixture has a concentration of water less than or equal to about 5 wt. % when the solvent is mixed with the compound of formula (II) and the NCS.

The present invention is based on the inventors' surprising finding that during the chlorination of the compound of formula (II) using NCS to synthesize the compound of formula (I), the water content of the reaction mixture is directly correlated with yield of the compound of formula (I). In particular, the inventors discovered that decreasing water content of the reaction mixture increases yield of the compound of formula (I). The inventors also discovered that when the water content of the reaction mixture is high, increasing the molar amount of NCS leads to an increased yield of the compound of formula (I).

The present invention is advantageous in that it is highly efficient. In particular, the processes disclosed herein provides a highly selective reaction exhibiting a high conversion rate, which results in higher yields, with reduced cost of production and simplified work-up. The present invention is also advantageous in that it minimizes related effluent disposal problems.

Water, even trace amounts, can react with NCS and the compound of formula (II) to form the des-chloro sulfoxide impurity, compound [241], in a strongly exothermic reaction:

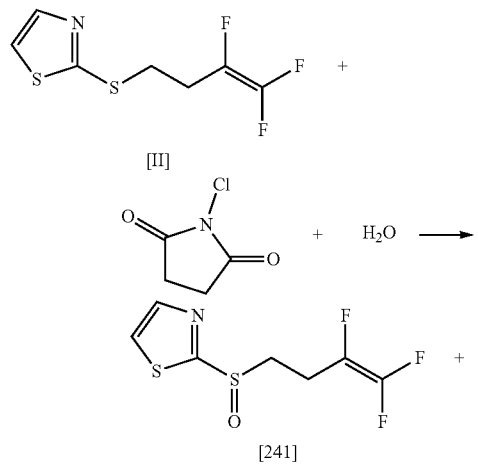

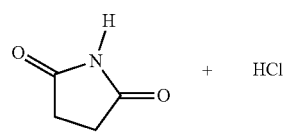

NCS, in the presence of water, can react with the compound of formula (II) to form impurities and over-chlorinated by-products such as compound [295] and compound [329].

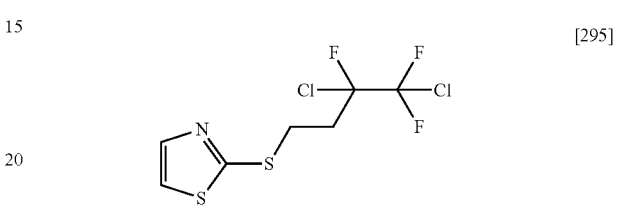

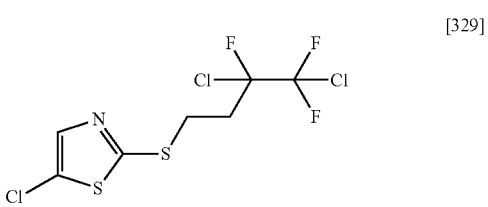

These side-reactions produce undesired products, leading to a reduced yield. Therefore, it is essential to reduce the water content of the reagents in the reaction. Preferably, the reaction mixture is substantially free of water.

In particular, the inventors discovered that an increase in water content leads to more exothermic reactions which reduces selectivity and yield of the desired product, i.e. the compound of formula (I). On the other hand, decreasing water content has the advantage of increasing selectivity, providing reduced corrosion in the reaction and high yield of the desired product, i.e. the compound of formula (I). In addition, reducing the exothermicity of the reaction brings operational advantages and reduces the risk of a thermal runaway reaction, which is a severe safety hazard.

The inventors also discovered that the presence of excess amount of water in the reaction reduces the selectivity of the reaction and increases the amount of impurities. In the presence of an excess amount of water, excess of NCS increases the yield of the desired compound (I).

The present invention provides an improved process for preparing the compound of formula (I)

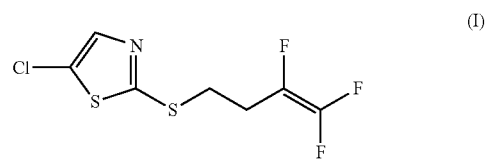 [SMILES: FC(F)=C(F)CCSc1ncc(Cl)s1]

which comprises reacting a compound of formula (II)

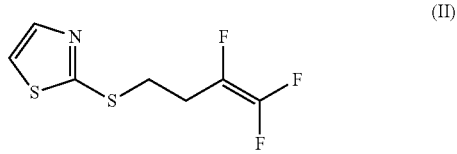 [SMILES: FC(F)=C(F)CCSc1nccs1]

with N-chlorosuccinimide (NCS) in the presence of water, the improvement comprising performing the step of reacting the compound of formula (II) with NCS in the presence of a reduced amount of water.

In some embodiments, the reduced amount of water is a concentration of water between 0% wt. and 5% wt. relative to the weight of the reaction mixture. In some embodiments, the reduced amount of water is a concentration of water less than or equal to 5% wt., or 4 wt. %, or 3 wt. %, or 2 wt. %, or 1 wt. %, or 0.5 wt. %, or 0.3 wt. %, or 0.1 wt. %, or 0.07 wt. %, or 0.05 wt. %, or 0.03 wt. %, or 0.01 wt. % relative to the weight of the reaction mixture.

In some embodiments, the reduced amount of water is a concentration of water between 0 wt. % and 7 wt. % relative to the weight of the compound of formula (II) in the reaction mixture. In some embodiments, the reduced amount of water is a concentration of water less than or equal to 7 wt. %, or 6 wt. %, or 5 wt. %, or 4 wt. %, or 3 wt. %, or 2 wt. %, or 1 wt. %, or 0.5 wt. %, or 0.3 wt. %, or 0.1 wt. %, or 0.07 wt. %, or 0.05 wt. %, or 0.03 wt. %, or 0.01 wt. % relative to the weight of the compound of formula (II) in the reaction mixture.

In some embodiments, the reduced amount of water is a concentration of water between 0 wt. % and 7 wt. % relative to the weight of NCS in the reaction mixture. In some embodiments, the reduced amount of water is a concentration of water less than or equal to 7 wt. %, or 6 wt. %, or 5 wt. %, or 4 wt. %, or 3 wt. %, or 2 wt. %, or 1 wt. %, or 0.5 wt. %, or 0.3 wt. %, or 0.1 wt. %, or 0.07 wt. %, or 0.05 wt. %, or 0.03 wt. %, or 0.01 wt. % relative to the weight of NCS in the reaction mixture.

In some embodiments, the molar ratio of NCS to the compound of formula (II) is from about 5:1 to about 1:5. In some embodiments, the molar ratio of NCS to the compound of formula (II) is from about 2:1 to about 1:2. In some embodiments, the molar ratio of NCS to the compound of formula (II) is from about 2:1 to about 1:1. In some embodiments, the improvement comprises using a molar ratio of NCS to the compound of formula (II) of about 1:1.

In some embodiments, the improvement further comprises performing the step of reacting the compound of formula (II) with NCS using an excess molar amount of NCS. In some embodiments, the molar ratio of NCS to the compound of formula (II) is from about 5:1 to about 1.01:1. In some embodiments, the molar ratio of NCS to the compound of formula (II) is from about 2:1 to about 1.01:1. In some embodiments, the molar ratio of NCS to the compound of formula (II) is from about 1.01:1 to about 1.2:1. In some embodiments, the molar ratio of NCS to the compound of formula (II) is from about 1.2:1 to about 2:1.

In some embodiments, the molar ratio of NCS to the compound of formula (II) is 1.05:1. In some embodiments, the molar ratio of NCS to the compound of formula (II) is 1.1:1. In some embodiments, the molar ratio of NCS to the compound of formula (II) is 1.2:1. In some embodiments, the molar ratio of NCS to the compound of formula (II) is 1.3:1. In some embodiments, the molar ratio of NCS to the compound of formula (II) is 1.4:1. In some embodiments, the molar ratio of NCS to the compound of formula (II) is 1.5:1. In some embodiments, the molar ratio of NCS to the compound of formula (II) is 1.6:1. In some embodiments, the molar ratio of NCS to the compound of formula (II) is 1.7:1. In some embodiments, the molar ratio of NCS to the compound of formula (II) is 1.8:1. In some embodiments, the molar ratio of NCS to the compound of formula (II) is 1.9:1. In some embodiments, the molar ratio of NCS to the compound of formula (II) is 2:1.

In some embodiments, the molar ratio of NCS to compound of formula (II) increases as the concentration of water in the reaction mixture increases.

In some embodiments, the weight ratio of NCS to the compound of formula (II) is from about 3:1 to about 1:8.5. In some embodiments, the weight ratio of NCS to the compound of formula (II) is from about 1.2:1 to about 1:3.4. In some embodiments, the weight ratio of NCS to the compound of formula (II) is from about 1.2:1 to about 0.6:1. In some embodiments, the weight ratio of NCS to the compound of formula (II) is from about 0.6:1.

In some embodiments, the improvement further comprises performing the step of reacting the compound of formula (II) with NCS using an excess molar amount of NCS. In some embodiments, the weight ratio of NCS to the compound of formula (II) is from about 3:1 to about 0.6:1. In some embodiments, the weight ratio of NCS to the compound of formula (II) is from about 1.2:1 to about 0.6:1. In some embodiments, the weight ratio of NCS to the compound of formula (II) is from about 0.6:1 to about 0.7:1. In some embodiments, the weight ratio of NCS to the compound of formula (I) is from about 1.2:1 to about 0.7:1.

In some embodiments, the weight ratio of NCS to the compound of formula (II) is 0.6:1. In some embodiments, the weight ratio of NCS to the compound of formula (II) is 0.7:1. In some embodiments, the weight ratio of NCS to the compound of formula (II) is 0.8:1. In some embodiments, the weight ratio of NCS to the compound of formula (II) is 0.9:1. In some embodiments, the weight ratio of NCS to the compound of formula (II) is 1:1. In some embodiments, the weight ratio of NCS to the compound of formula (II) is 1.1:1. In some embodiments, the weight ratio of NCS to the compound of formula (II) is 1.2:1.

In some embodiments, the weight ratio of NCS to the compound of formula (II) increases as the concentration of water in the reaction mixture increases.

In some embodiments, the concentration of water in the reaction mixture is less than 1 wt. % relative to the weight of NCS in the reaction mixture, and the weight ratio of NCS to the compound of formula (II) is from about 0.6:1 to about 0.7:1.

In some embodiments, the concentration of water in the reaction mixture is less than 1 wt. % relative to the weight of the compound of formula (I) in the reaction mixture, and the weight ratio of NCS to the compound of formula (II) is from about 0.6:1 to about 0.7:1.

In some embodiments, the reaction mixture has a water content of less than 1 wt. % relative to the weight of NCS in the reaction mixture, and the molar ratio of NCS to the compound of formula (II) is from about 1:1 to about 1.2:1.

In some embodiments, the reaction mixture has a water content of less than 1 wt. % relative to the weight of the compound of formula (II) in the reaction mixture, and the molar ratio of NCS to the compound of formula (II) is from about 1:1 to about 1.2:1.

In some embodiments, the reaction mixture has a water content of between 1 wt. % to 7 wt. % relative to the weight of NCS in the reaction mixture, and the weight ratio of NCS to the compound of formula (II) is from about 0.7:1 to about 1:1.

In some embodiments, the reaction mixture has a water content of between 1 wt. % to 7 wt. % relative to the weight of the compound of formula (II) in the reaction mixture, and the weight ratio of NCS to the compound of formula (II) is from about 0.7:1 to about 1:1.

In some embodiments, the reaction mixture has a water content of between 1 wt. % to 7 wt. % relative to the weight of NCS in the reaction mixture, and the molar ratio of NCS to the compound of formula (II) is from about 1.2:1 to about 1.7:1.

In some embodiments, the reaction mixture has a water content of between 1 wt. % to 7 wt. % relative to the weight of the compound of formula (II) in the reaction mixture, and the molar ratio of NCS to the compound of formula (II) is from about 1.2:1 to about 0.71.

In some embodiments, the reduced amount of water is achieved by drying the compound of formula (II) prior to performing the reacting step. In some embodiments, the reduced amount of water is achieved by drying the NCS prior to performing the reacting step.

Drying may be accomplished by distillation or by using drying agent(s) (e.g. molesieves or $MgSO_4$) which bind or react with the water.

In some embodiments, the reduced amount of water is achieved by adding a drying agent or water scavenger agent. In some embodiments, the drying agent and/or water scavenger agent is selected from molecular sieves and inorganic salts. In some embodiments, the inorganic salts are selected from calcium chloride, magnesium sulfate and sodium sulfate.

In some embodiments, the dried compound of formula (II) has a water content from about 0 wt. % to about 0.2 wt. %.

In some embodiments, the dried NCS has a water content from about 0 wt. % to about 2 wt. %.

In some embodiments, the reduced amount of water is achieved by selecting a batch of NCS with low water content.

In some embodiments, the NCS has a water content from about 0 wt. % to about 5 wt. % before drying. In some embodiments, the NCS has a water content from about 1 wt. % to about 5 wt. % before drying. In some embodiments, the NCS has a water content of 4.8 wt. % or less before drying.

In some embodiments, the improvement comprises performing the reaction free of solvent. In some embodiments, the improvement comprises performing the reaction in neat conditions.

In some embodiments, the improvement comprises reacting a compound of formula (II) with NCS in the presence of at least one solvent. In some embodiments, the improvement comprises reacting a compound of formula (II) with NCS in the presence of two solvents.

In some embodiments, the reduced amount of water is achieved by drying the solvent prior to using it in the reaction mixture. In some embodiments, the reduced amount of water is achieved by selecting a low water content solvent. In some embodiments, the reduced amount of water is achieved by selecting a batch of solvent with low water content.

In some embodiments, the improvement comprises dissolving or suspending the NCS in the solvent to form a solution or suspension before reacting the NCS with the compound of formula (II).

In some embodiments, the improvement comprises a step of drying the solution or suspension prior to reacting the NCS with the compound of formula (II).

In some embodiments, the dried solution or suspension has a water content from about 0 wt. % to about 2 wt. % based on the total weight of the solution or suspension. In some embodiments, the dried solution or suspension has a water content between 0 wt. % to 1.5 wt. % based on the total weight of the solution or suspension. In some embodiments, the dried solution or suspension has a water content between 0 wt. % to 1 wt. % based on the total weight of the solution or suspension. In some embodiments, the dried solution or suspension has a water content between 0 wt. % to 0.5 wt. % based on the total weight of the solution or suspension. In some embodiments, the dried solution or suspension has a water content of less than about 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. % 1.5 wt. %, 1.6 wt. %, 1.7 wt. %, 1.8 wt. %, 1.9 wt. % or 2 wt. %, based on the total weight of the solution or suspension.

In some embodiments, the solvent is a polar solvent. In some embodiments, the solvent is a non-polar solvent. In some embodiment, the at least one solvent is a mixture of at least one polar solvent and at least one non-polar solvent.

In some embodiments, the solvents in the reaction mixture have a dielectric constant ($\varepsilon$) of about $\varepsilon=2\text{-}40$.

Polar solvent may include but are not limited to nitriles, amides, ethers, nitro-groups containing solvents, chlorinated solvents, and combination thereof.

In some embodiments, the polar solvent is a nitrile solvent. In some embodiments, the nitrile solvent is a $C_1$-$C_6$ nitrile. In some embodiments, the nitrile solvent is acetonitrile. In some embodiments, the nitrile solvent is isobutyronitrile. In some embodiments, the nitrile solvent is a combination of acetonitrile and isobutyronitrile.

In some embodiments, the polar solvent is an amide solvent. In some embodiments, the amide solvent is dimethylformamide.

In some embodiments, the polar solvent is a chlorinated polar solvent. In some embodiments, the chlorinated solvent is chloroform. In some embodiments, the chlorinated solvent is methylene chloride.

Non-polar solvents may include but are not limited to aliphatic hydrocarbons, or aromatic hydrocarbons, or chlorinated hydrocarbon and combination thereof.

In some embodiments, the non-polar solvent is a chlorinated non-polar solvent. In some embodiments, the chlorinated non-polar solvent is carbon tetrachloride. In some embodiments, the chlorinated non-polar solvent is monochlorobenzene.

In some embodiments, the non-polar solvent is an aromatic non-polar solvent. In some embodiments, the aromatic non-polar solvent is toluene.

In some embodiments, the non-polar solvent is an aliphatic hydrocarbon non-polar solvent. In some embodiments, the aliphatic hydrocarbon non-polar solvent is hexane.

In some embodiments, the improvement comprises performing the reaction at a temperature of from about 0° C. to about 150° C. In some embodiments, the improvement comprises performing the reaction at a temperature of about 30° C.-80° C. In some embodiments, the improvement comprises performing the reaction at a temperature of about 40° C.-60° C. In some embodiments, the improvement comprises performing the reaction at a temperature of about 50° C.

In some embodiments, the improvement comprises obtaining a conversion rate of the compound of formula (II) to the compound of formula (I) of at least 50%, or 60%, or 70%, or 80%, or 90%, or 95%, or 99%. In some embodiments, the improvement comprises obtaining a conversion rate of the compound of formula (II) to the compound of formula (I) of more than 90%, or 95%, or 99%.

In some embodiments, the improvement further comprises a step of removing succinimide from the reaction mixture to obtain the compound of formula (I). In some embodiments, the improvement further comprises a step of removing succinimide and the solvent(s) from the reaction mixture to obtain the compound of formula (I). In some embodiments, the solvent(s) are removed prior to the removal of the succinimide. In some embodiments, the succinimide is removed prior to the removal of the solvent(s). In some embodiments, the succinimide is removed by filtration. In some embodiments, the solvent is removed by evaporation.

The present invention also provides a process for recovering NCS comprising reacting the succinimide resulting from any one of the improved processes disclosed herein with a chlorinating agent.

In some embodiments, the process comprises reacting the succinimide with a chlorinating agent in the presence of PH adjuster.

PH adjusters may include but are not limited to an acid and a base.

In some embodiments, the PH adjuster is buffer. In some embodiments, the buffer is a phosphonate, phosphate, carbonate, acetate, oxalate, or formate-based buffer.

Acids may include but are not limited to organic and inorganic acid.

Organic acids may include but are not limited to formic, oxalic, carbonic, acetic, propionic, benzoic, and citric acid.

Inorganic acid may include but are not limited to sulfuric, sulfonic, sulfinic, phosphoric, and phosphonic acid.

Bases may include but are not limited to organic and inorganic bases.

Organic bases may include but are not limited to sodium, potassium, calcium and magnesium salts of the aforementioned organic acids in different deprotonation levels, e.g. sodium carbonate and sodium bicarbonate.

Inorganic bases may include but are not limited to sodium, potassium, calcium and magnesium salts of the aforementioned inorganic acids in different deprotonation levels, e.g. monosodium phosphate, disodium phosphate, and trisodium phosphate, and sodium hydroxide, potassium hydroxide, calcium hydroxide and magnesium hydroxide.

Chlorinating agents may include but are not limited to chlorine ($Cl_2$), hypochlorite, hypochloric acid, sulfuryl chloride or thionyl chloride. In some embodiments, the process for the recovering of NCS is conducted at a temperature of less than about 50° C.

In some embodiments, the process for the recovery of NCS is conducted at pH of about 2-7.

The present invention also provides a process of preparing a compound of formula (I)

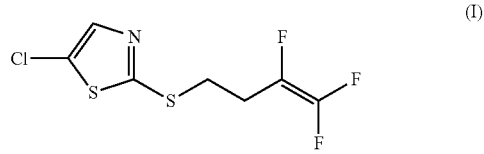 [SMILES: FC(F)=C(F)CCSc1ncc(Cl)s1]

comprising reacting a compound of formula (II)

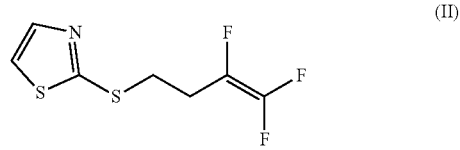 [SMILES: FC(F)=C(F)CCSc1nccs1]

with N-chlorosuccinimide (NCS) in a low water content reaction mixture, wherein the process comprises (i) obtaining a low water content compound of formula (II), and/or (ii) obtaining a low water content NCS.

In some embodiments, the low water content compound of formula (II) is obtained by drying the compound of formula (II) prior to reacting it with the NCS. In some embodiment, the low water content NCS is obtained by drying the NCS prior to reacting it with the compound of formula (II).

In some embodiments, the low water content NCS is obtained by selecting a batch of NCS with low water content.

In some embodiments, the obtained compound of formula (II) has a water content from about 0 wt. % to about 0.2 wt. % based on the total weight of the compound.

In some embodiments, the obtained compound of NCS has a water content from about 0 wt. % to about 2 wt. % based on the total weight of the compound.

In some embodiments, the low water content reaction mixture further comprises at least one solvent and the process further comprises obtaining a low water content solvent. In some embodiments, the low water content solvent is obtained by drying the solvent prior to using it in the reaction mixture. In some embodiment, the low water content solvent is obtained by selecting a solvent or a batch of a solvent with low water content.

The present invention also provides a method of increasing yield of a compound of formula (I) in a process of synthesizing the compound of formula (I) which involves reacting a compound of formula (II) with NCS in the presence of water, wherein the method comprises performing the step of reacting the compound of formula (II) with NCS in the presence of less water so as to increase the yield of the compound of formula (I) relative to a process where more water is present during the reacting step.

In some embodiments, the method comprises drying the compound of formula (II) prior to performing the reacting step. In some embodiments, the method comprises drying the NCS prior to performing the reacting step. In some embodiment, the NCS is dissolved or suspended in a solvent and the method comprises drying the solution or suspension prior to performing the reacting step.

In some embodiments, the method comprises selecting a low water content batch of NCS. In some embodiments, the method comprises selecting a low water content solvent. In some embodiments, the method comprises selecting a batch of solvent with low water content.

In some embodiments, the method comprises drying the reaction equipment prior to use.

In some embodiments, the water content of the reaction mixture is less than or equal to 5 wt. % relative to the weight of the reaction mixture. In some embodiments, the water content of the reaction mixture is less than or equal to 5 wt. %, or 4 wt. %, or 3 wt. %, or 2 wt. %, or 1 wt. %, or 0.5 wt. %, or 0.3 wt. %, or 0.1 wt. %, or 0.07 wt. %, or 0.05 wt. %, or 0.03 wt. %, or 0.01 wt. % relative to the total weight of the reaction mixture.

In some embodiments, the method increases the yield of the compound of formula (I) by at least 10%. In some embodiments, the method increases the yield of the compound of formula (I) by at least 25%. In some embodiments, the method increases the yield of the compound of formula (I) by at least 50%. In some embodiments, the method increases the yield of the compound of formula (I) by at least 60%. In some embodiments, the method increases the yield of the compound of formula (I) by at least 70%. In some embodiments, the method increases the yield of the compound of formula (I) by at least 80%. In some embodiments, the method increases the yield of the compound of formula (I) by at least 90%. In some embodiments, the method increases the yield of the compound of formula (I) by 100% or more.

In some embodiments, the yield of the compound of formula (I) is greater than or equal to 70%. In some embodiments, the yield of the compound of formula (I) is greater than or equal to 80%. In some embodiments, the yield of the compound of formula (I) is greater than or equal to 85%. In some embodiments, the yield of the compound of formula (I) is greater than or equal to 90%. In some embodiments, the yield of the compound of formula (I) is greater than or equal to 95%.

The present invention also provides an improved process for preparing a compound of formula (I)

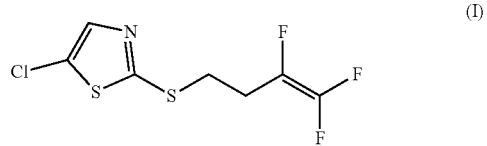 [SMILES: FC(F)=C(F)CCSc1ncc(Cl)s1]

(I)

which comprises reacting a compound of formula (II)

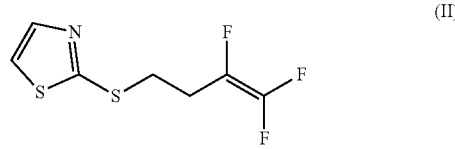 [SMILES: FC(F)=C(F)CCSc1nccs1]

(II)

with N-chlorosuccinimide (NCS) in the presence of water, the improvement comprising performing the step of reacting the compound of formula (II) with an excess molar amount of NCS.

It was discovered that in reaction mixtures comprising water, adding excess of NCS increases the yield of the desired compound (I).

In some embodiments, the water content of the reaction mixture is less than 5 wt. % relative to the total weight of the reaction mixture. In some embodiments, the water content of the reaction mixture is less than 7 wt. % relative to the weight of the NCS. In some embodiments, the water content of the reaction mixture is less than 7 wt. % relative to the weight of the compound of formula (II).

In some embodiments, the water content of the reaction mixture is greater than 5 wt. % relative to the total weight of the reaction mixture. In some embodiments, the water content of the reaction mixture is greater than 7 wt. % relative to the weight of the NCS. In some embodiments, the water content of the reaction mixture is greater than 7 wt. % relative to the weight of the compound of formula (II).

In some embodiments, the molar ratio of NCS to the compound of formula (II) is from about 5:1 to about 1.01:1. In some embodiments, the molar ratio of NCS to the compound of formula (II) is from about 2:1 to about 1.01:1. In some embodiments, the molar ratio of NCS to the compound of formula (II) is from about 2:1 to about 1.2:1.

In some embodiments, the molar ratio of NCS to the compound of formula (II) is 1.05:1. In some embodiments, the molar ratio of NCS to the compound of formula (II) is 1.1:1. In some embodiments, the molar ratio of NCS to the compound of formula (II) is 1.2:1. In some embodiments, the molar ratio of NCS to the compound of formula (II) is 1.3:1. In some embodiments, the molar ratio of NCS to the compound of formula (II) is 1.41. In some embodiments, the molar ratio of NCS to the compound of formula (II) is 1.5:1. In some embodiments, the molar ratio of NCS to the compound of formula (II) is 1.6:1. In some embodiments, the molar ratio of NCS to the compound of formula (II) is 1.7:1. In some embodiments, the molar ratio of NCS to the compound of formula (II) is 1.8:1. In some embodiments, the molar ratio of NCS to the compound of formula (II) is 1.9:1. In some embodiments, the molar ratio of NCS to the compound of formula (II) is 2:1.

In some embodiments, the molar ratio of NCS to the compound of formula (II) increases as the concentration of water in the reaction mixture increases.

In some embodiments, the weight ratio of NCS to the compound of formula (II) is from about 3:1 to about 0.6:1. In some embodiments, the weight ratio of NCS to the compound of formula (II) is from about 1.2:1 to about 0.6:1. In some embodiments, the weight ratio of NCS to the compound of formula (II) is from about 1.2:1 to about 0.7:1.

In some embodiments, the weight ratio of NCS to the compound of formula (II) is 0.6:1. In some embodiments, the weight ratio of NCS to the compound of formula (II) is 0.7:1. In some embodiments, the weight ratio of NCS to the compound of formula (II) is 0.8:1. In some embodiments, the weight ratio of NCS to the compound of formula (II) is 0.9:1. In some embodiments, the weight ratio of NCS to the compound of formula (II) is 1:1. In some embodiments, the weight ratio of NCS to the compound of formula (II) is 1.1:1. In some embodiments, the weight ratio of NCS to the compound of formula (II) is 1.2:1.

In some embodiments, the weight ratio of NCS to the compound of formula (II) increases as the concentration of water in the reaction mixture increases.

The subject invention also provides a method of increasing yield of a compound of formula (I) in a process of synthesizing the compound of formula (I) which involves reacting a compound of formula (II) with NCS in the presence of water, wherein the method comprises adding excess molar amount of NCS to the reaction mixture.

The subject invention also provides a compound of formula (I)

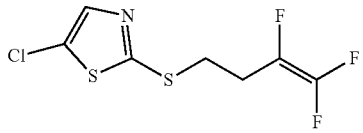

prepared using any one of the processes or methods disclosed herein.

The present invention also provides a process for preparing a compound of formula (III)

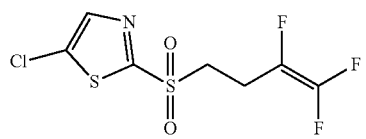

comprising converting the compound of formula (I) prepared according to any one of the processes disclosed herein.

A process for preparing the compound of formula (III) comprising converting the compound having the structure (I) is described in U.S. Patent Application Publication No. 2006/0004196, the contents of which is hereby incorporated by reference.

The present invention also provides a compound of formula (III)

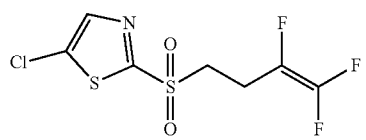

prepared using any one of the processes disclosed herein.

The prevent invention also provides a compound of formula (III)

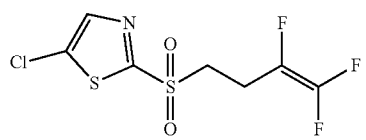

prepared using a compound of formula (I)

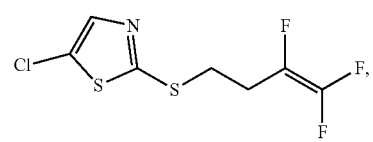

wherein the compound of formula (I) is prepared using any one of the processes or methods disclosed herein.

Each embodiment disclosed herein is contemplated as being applicable to each of the other disclosed embodiments. Thus, all combinations of the various elements described herein are within the scope of the invention. In addition, the elements recited in process embodiments can be used in the method embodiments described herein and vice versa.

This invention will be better understood by reference to the Experimental Details which follow, but those skilled in the art will readily appreciate that the specific examples detailed are only illustrative of the invention as described more fully in the claims which follow thereafter. The invention is illustrated by the following examples without limiting it thereby.

EXPERIMENTAL SECTION

Reactions in Different Solvents Under Dry Conditions:
General Procedure of Drying of the Compound of Formula (II) with MeCN:

50 g of MeCN (Karl Fischer analysis: 0.03 wt. % water) was added to 100 g crude of the compound of formula (II) (purity: 93.0% by quantitative analysis vs. standard, Karl Fischer analysis: 0.22 wt. % water). All volatiles were removed in vacuum (30 mbar, 50° C.) to receive 95 g dry compound of formula (II). This procedure reduced the water content to 0.05-0.09 wt. % (Karl Fischer analysis). Quantitative analysis gave 94.1% of the compound of formula II.

Example 1: Reaction in Acetonitrile (MeCN)

300 g of MeCN (Karl Fischer analysis: 0.03 wt. % water) was added to a 1 L flask and heated to 50° C. Afterwards 58.6 g of NCS (purity: 95% by quantitative analysis vs. standard; water content 4.8 wt. %, 417 mmol, 1.07 equiv.) were added to the heated solvent under stirring to receive a clear solution. All volatiles were removed in vacuo using a rotavapor (up to 20-30 mbar and 60° C.). Afterwards, 300 g of MeCN were added and evaporated again to ensure sufficient dryness. The residual NCS was then dissolved or suspended in overall 300 g MeCN (Karl Fischer analysis: 0.03 wt. % water) and transferred to a 1 L reactor and heated to 50° C. To this mixture, 92.8 g of dried compound of formula (II) (Purity 94.1%, 388 mmol, 1.00 equiv.) was added dropwise over 10 min at 50° C. During the addition of the compound of formula (II), a mild exothermic reaction was observed ($\Delta T$=ca. 1-2° C.). The progress of the reaction was followed by GC analysis. After 90 minutes, the signal for the compound of formula (II) disappeared (GC: the compound of formula (I)=99.2 Area % and compound [329]=0.8 Area %). The reaction mixture was cooled to 0° C., solids were filtered off, and the filter cake washed with ca. 50 g cold MeCN to receive 477.6 g of combined organic phase (mother liquor and wash). Quantitative analyses (vs. standard) of this mixture gave the following composition: 19.1 wt. % of the compound of formula (I); 0.03 wt. % of the compound of formula (II), and 0.29 wt. % of compound [241]. This corresponds to 352 mmol of the compound of formula (I) and a yield of 91%.

Example 2: Reaction in Chloroform (HCCl$_3$)

300 g of chloroform and 58.6 g of NCS (purity: 95% by quantitative analysis vs. standard; water content 4.8 wt. %, 417 mmol, 1.07 equiv.) were added to a 1 L flask and all volatiles were removed in vacuo using a rotavapor (up to 20-30 mbar and 60° C.). Afterwards, 600 g of chloroform were added and 300 g were evaporated again to ensure sufficient dryness. The residual NCS suspension was then transferred to a 1 L reactor, for complete transfer of all solids additional 50 g chloroform (Karl Fischer analysis: 0.04 wt. %) were used and the resulting mixture was heated to 70° C. To this mixture, 92.8 g of dried compound of formula (II) (Purity 94.1%, 388 mmol, 1.00 equiv.) was added dropwise. No exothermic effect could be observed during the addition. The reaction mixture was stirred at this temperature and the progress of the reaction was followed by periodic GC sampling. After 3.5 hours reaction time GC analysis showed: the compound of formula (II)=0.5 Area %; the compound of formula (I)=98.0 Area % and compound [329]=0.9 Area %. The reaction mixture was cooled to 0° C. and solids were filtered off and the filter cake washed with ca. 50 g cold chloroform to receive 446.3 g of combined organic phase (mother liquor and wash). Quantitative analyses (vs. standard) of this mixture gave the following composition: 20.2 wt. % of the compound of formula (I); 0.42 wt. % of the compound of formula (II) and 0.007 wt. % of compound [241]. This corresponds to 347 mmol of the compound of formula (I) and a yield of 89%.

Example 3: Reaction in Isobutyronitrile (IBN)

600 g of IBN (Karl Fischer analysis: 0.03 wt. % water), 58.6 g of NCS (purity: 95% by quantitative analysis vs. standard; 417 mmol, 1.07 equiv.) were added stirred of molecular sieves 4 Å over the weekend. The reaction mixture was filtered, added to a 1 L reactor and heated to 50° C. To this mixture, 92.8 g of dried compound of formula (II) (Purity 94.1%, 388 mmol, 1.00 equiv.) was added dropwise. No exothermic reaction could be observed during the addition. After 1 hour stirring, the reaction temperature was increased to 60° C., and after further 2.5 hours, additional 4.6 g of NCS (purity: 95% by quantitative analysis vs. standard, 4.8 wt. % water; 33 mmol, 0.09 equiv.) were added. After stirring the mixture at 60° C. for further 30 min, it was cooled to 0° C. and a GC sample was taken (GC analysis: the compound of formula (II)=0.4 Area %; the compound of formula (I)=98.4 Area % and compound [329]=0.9 Area %). All solids were filtered off and the filter cake washed with ca. 50 g cold IBN to receive 650 g of combined organic phase (mother liquor and wash). Quantitative analyses (vs. standard) of this mixture gave the following composition: 13.1 wt. % of the compound of formula (I); 0.5 wt. % of the compound of formula (II) and 0.36 wt. % of compound [241]. This corresponds to 328 mmol of the compound of formula (I) and a yield of 85%.

Example 4: Reaction in a Mixture of DMF (Dimethylformamide) and Toluene 150 g of toluene and 58.6 g of NCS (purity: 95% by quantitative analysis vs. standard; 417 mmol, 1.07 equiv.) were added to a 1 L flask and all volatiles were removed in vacuo using a rotavapor (up to 20-30 mbar and 60° C.). To the dry residue, additional 150 g of toluene were added and subsequently evaporated at the rotavapor. Subsequently, additional 250 g toluene were added to the dry residue, 50 g of volatiles were evaporated and the resulting suspension was transferred to a 1 L reactor. The mixture was heated to 60° C. and 100 g of DMF were added (0.5 wt. % water) to receive a clear solution. To this mixture, 92.8 g of dried compound of formula (II) (Purity 94.1%, 388 mmol, 1.00 equiv.) was added dropwise. Due to a relatively large rise in temperature (exothermic reaction) of 8° C., the dropwise addition was performed over 30 min. After 2 hours of stirring at 60° C., an additional 16.5 g of NCS (purity: 95% by quantitative analysis vs. standard, 4.8 wt. % water according to Karl Fischer analysis; 117 mmol, 0.30 equiv.) were added. After stirring the mixture at 60° C. for another 60 minutes, the mixture was cooled to 0° C. and a GC sample was taken. The GC analysis after 2.5 h showed the following picture: the compound of formula (II)=not detected; the compound of formula (I)=94.3 Area % and compound [329]=5.2 Area %. At 0° C., all solids were filtered off and the filter cake washed with ca. 50 g cold toluene to receive 479 g of combined organic phase (mother liquor and wash). Quantitative analyses (vs. standard) of this mixture gave the following composition: 16.7 wt. % of the compound of formula (I); 0.03 wt. % of the compound of formula (II) and 0.17 wt. % of compound [241]. This corresponds to 308 mmol of the compound of formula (I) and a yield of 79%.

Example 5: Reaction in a Mixture of Isobutyronitrile (IBN) and Chlorobenzene (MCB)

200 g of MCB and 59.0 g of NCS (purity: 95% by quantitative analysis vs. standard; 419 mmol, 1.07 equiv.) were added to a 1 L flask and all volatiles were removed in vacuo using a rotavapor (up to 10-20 mbar and 60° C.). To the dry residue, additional 250 g of MCB were added, 50 g of volatiles were evaporated and the resulting suspension was transferred to a 1 L reactor. 100 g of IBN (0.25 wt. % water content acc. to Karl Fischer) were added to the reactor and the reaction mixture was heated to 50° C. To this mixture, 90 g of dried compound of formula (II) (Purity 98%, 392 mmol, 1.00 equiv.) was added dropwise and the reaction mixture was stirred at 50° C. The GC analysis after 4 h showed the following composition: the compound of formula (II)=0.5 Area %; the compound of formula (I)=97.0 Area % and compound [329]=1.6 Area %. The reaction mixture was cooled to ambient temperature and washed three times, each time with 200 g of water. The combined water phases were then extracted with 200 g of MCB. The organic phases were combined and all volatiles were removed in vacuum using a rotavapor (ca 10 mbar and 60° C.) to receive 106 g residue. Quantitative analyses (vs. standard) of this mixture gave the following composition: 83.0 wt. % of the compound of formula (I); 0.24 wt. % of the compound of formula (II) and 2.95 wt. % of compound [241]. This corresponds to 339 mmol of the compound of formula (I) and a yield of 86%.

Example 6: Reaction in a Mixture of Acetonitrile (MeCN) and Chlorobenzene (MCB)

13000 g of MCB and 2915 g of NCS (purity: 95.7% by quantitative analysis vs. standard, 20.892 mol, 1.04 equiv.) were added to a 25 L reactor equipped with a Dean Stark apparatus. The mixture was dried by azeotropic distillation until no water was collected anymore in the distillate. The water, which was obtained in this azeotropic distillation was discarded. Subsequently, additional 3100 g of MCB were distilled out to ensure a high level of dryness. Afterwards, the reaction mixture was allowed to reach ambient temperature under nitrogen flushing (not to add additional water to the system) and 3500 g MeCN (0.03 wt. % water according to Karl Fisher analysis) were added. This mixture was heated to 50° C. and 4600 g of the compound of formula (II)(98.1 wt. %, 20.033 mol, 1.00 equiv., 0.13 wt. % water) were added slowly, over 1 h. The end of reaction was observed after ca. 3 h after full addition. Volatiles were partially removed from the reaction mixture by evaporation (up to 53 mbar, 55° C.). The reaction mixture was washed 3 times, each time with 10 kg of water, and the residual volatiles have been removed (up to 20 mbar, 62° C.) to receive 5367 g of the compound of formula (I) crude (91.7 wt. %). Quantitative analyses (vs. standard) of this mixture gave the following composition: 91.7 wt. % of the compound of formula (I); 0.3 wt. % of the compound of formula (II) and 0.54 wt. % of compound [241]. This corresponds to 18.951 mol of the compound of formula (I) and a yield of 95%.

Comparative Example Reactions in MeCN Under "Wet" Conditions

Example 7: Drying of the Compound of Formula (II), No Drying of the NCS/MeCN Mixture, Addition of 1.5 g of Water, No Additional Feed of NCS (as Compared to Example 8)

300 g of MeCN (Karl Fischer analysis: 0.03 wt. % water) and 1.5 g water were added to a 1 L reactor and heated to 50° C. Afterwards, 58.6 g of NCS (purity: 95% by quantitative analysis vs. standard; 4.8 wt. % water according to Karl Fischer analysis, 417 mmol, 1.07 equiv.) were added to the heated mixture under stirring to receive a clear solution. To this mixture, 92.8 g of dried compound of formula (II) (Purity 94.1%, 388 mmol, 1.00 equiv.) was added dropwise. After addition of ca. 10 g of the compound of formula (II), a strong exothermic reaction was observed ($\Delta T$=ca. 14° C.). Therefore, an overall addition time of ca. 30 min was chosen. During this time, a maximum temperature of 64° C. was observed. After full addition, the progress of the reaction was followed by GC analysis. The reaction stalled after 30 min as observed by GC analysis (after 60 min, GC: the compound of formula (II)=61.6 Area %; the compound of formula (I)=38.8 Area % and compound [329]=0.5 Area %). The reaction mixture was cooled to 0° C., solids were filtered off, and the filter cake washed with ca. 50 g cold MeCN to receive 444 g of combined organic phase (mother liquor and wash). Quantitative analyses (vs. standard) of this mixture gave the following composition: 6.7 wt. % of the compound of formula (I); 12.4 wt. % of the compound of formula (II). This corresponds to 115 mmol of the compound of formula (I) and a yield of 30%.

Example 8: Drying of the Compound of Formula (II), No Drying of the NCS/MeCN Mixture, Addition of 1.5 g Water, with Additional Feed of NCS (as Compared to Example 7)

300 g of MeCN (Karl Fischer analysis: 0.03 wt. % water) and 1.5 g water were added to a 1 L reactor and heated to 50° C. Afterwards 58.6 g of NCS (purity: 95% by quantitative analysis vs. standard; 4.8 wt. % water according to Karl Fischer analysis, 417 mmol, 1.07 equiv.) were added to the heated mixture under stirring to receive a clear solution. To this mixture, 92.8 g of dried compound of formula (II) (Purity 94.1%, 388 mmol, 1.00 equiv.) was added dropwise. After addition of ca. 10 g of the compound of formula (II), a strong exothermic reaction was observed ($\Delta T$=ca. 13° C.). Therefore, an overall addition time of ca. 30 min was chosen. During this time, a maximum temperature of 63° C. was observed. After full addition, the progress of the reaction was followed by GC analysis. The reaction stalled after 30 min as observed by GC analysis (after 60 min GC: the compound of formula (II)=55.5 Area %; the compound of formula (I)=44.3 Area % and compound [329]=0.2 Area %). After 90 minutes, additional 26.0 g of NCS (purity: 95% by quantitative analysis vs. standard; 4.8 wt. % water according to Karl Fischer analysis, 185 mmol, 0.48 equiv.) were added and the reaction mixture was stirred for 30 more minutes. GC analysis showed almost full conversion after this time (after 120 min GC: the compound of formula (I)=0.3 Area %; the compound of formula (II)=95.4 Area % and compound [329]=0.9 Area %). The reaction mixture was cooled to 0° C., solids were filtered off, and the filter cake washed with ca. 50 g cold MeCN to receive 454 g of combined organic phase (mother liquor and wash). Quantitative analyses (vs. standard) of this mixture gave the following composition: 17.5 wt. % of the compound of formula (I); 0.04 wt. % of the compound of formula (II). This corresponds to 306 mmol of the compound of formula (I) and a yield of 79%.

Example 9: Drying of the Compound of Formula (II), No Drying of the NCS/MeCN Mixture, Addition of 3.0 g Water, Additional Feed of NCS 300 g of MeCN (Karl Fischer analysis: 0.03 wt. % water) and 3.0 g water were added to a 1 L reactor and heated to 50° C. Afterwards, 58.6 g of NCS (purity: 95% by quantitative analysis vs. standard: 4.8 wt. % water according to Karl Fischer analysis, 417 mmol, 1.07 equiv.) were added to the heated solvent under stirring to receive a clear solution. To this mixture, 92.8 g of dried compound of formula (II) (Purity 94.1%, 388 mmol, 1.00 equiv.) was added dropwise. After addition of ca. 10 g of the compound of formula (II) a strong exothermic reaction was observed ($\Delta T$=ca. 7° C.). Therefore, an overall addition time of ca. 40 min was chosen. During this time, a maximum temperature of 58° C. was observed. After full addition, the progress of the reaction was followed by GC analysis. The reaction stalled after 30 min as observed by GC analysis (after 60 min GC: the compound of formula (II)=89.6 Area %; the compound of formula (I)=9.4 Area % and compound [329]=1.0 Area %). After 90 minutes, additional 54.5 g of NCS (purity: 95% by quantitative analysis vs. standard; 4.8 wt. % water according to Karl Fischer analysis, 388 mmol, 1.00 equiv.) were added portion-wise over ca. 30 minutes not to exceed 60° C. After ca. 30-40 minutes after addition, GC analysis showed almost full conversion of the reaction (GC: the compound of formula (II)=0.4 Area %; the compound of formula (I)=84.0 Area % and compound [329]=13.0 Area %). The reaction mixture was cooled to 0° C., solids were filtered off, and the filter cake washed with ca. 50 g cold MeCN to receive 494 g of combined organic phase (mother liquor and wash). Quantitative analyses (vs. standard) of this mixture gave the following composition: 8.2 wt. % of the compound of formula (I); 0.04 wt. % of the compound of formula (II); 0.004 wt. % of compound [241]. This corresponds to 156 mmol of the compound of formula (I) and a yield of 40%.

Example 10: Drying of the Compound of Formula (II), No Drying of the NCS/MeCN Mixture, Addition of 4.5 g Water, Additional Feed of NCS 300 g of MeCN (Karl Fischer analysis: 0.03 wt. % water) and 4.5 g water were added to a 1 L reactor and heated to 50° C. Afterwards, 58.6 g of NCS (purity: 95% by quantitative analysis vs. standard; 4.8 wt. % water according to Karl Fischer analysis, 417 mmol, 1.07 equiv.) were added to the heated solvent under stirring to receive a clear solution. To this mixture, 92.8 g of dried compound of formula (II) (Purity 94.1%, 388 mmol, 1.00 equiv.) was added dropwise. After addition of ca. 13 g of the compound of formula (II), a strong exothermic reaction was observed (ΔT=ca. 8° C.). Therefore, an overall addition time of ca. 50 min was chosen. During this time, a maximum temperature of 60° C. was observed. After full addition, the progress of the reaction was followed by GC analysis. The reaction stalled after 30 min as observed by GC analysis (after 30 min GC: the compound of formula (II)=95.1 Area %; the compound of formula (I)=4.90 Area % and compound [329]=0.0 Area %). After 90 minutes, additional 58.6 g of NCS (purity: 95% by quantitative analysis vs. standard; 4.8 wt. % water according to Karl Fischer analysis, 417 mmol, 1.07 equiv.) were added portion-wise over ca. 30 minutes not to exceed 60° C. After ca. 30-40 minutes after addition, GC analysis showed almost full conversion of the reaction (after 40 min GC: the compound of formula (II)=0.2 Area %; the compound of formula (I)=80.5 Area % and compound [329]=14.6 Area %). The reaction mixture was cooled to 0° C., solids were filtered off, and the filter cake washed with ca. 50 g cold MeCN to receive 490 g of combined organic phase (mother liquor and wash). Quantitative analyses (vs. standard) of this mixture gave the following composition: 10.1 wt. % of the compound of formula (I); 0.08 wt. % of the compound of formula (II); 0.01 wt. % compound [241]. This corresponds to 191 mmol of the compound of formula (I) and a yield of 49%.

Discussion

There is a need to develop an efficient and selective process for synthesizing the compound of formula (I).

The process described herein is carried out in a substantially water-free environment under ambient pressure, with easily handled material, in a process that is highly efficient, low-cost, and environmentally friendly. These advantages are not exhibited by any current synthesis method for the compound of formula (I). It has been found that the synthesis of the compound of formula (I) using NCS in a substantially water-free environment can significantly improve the conversion rate and isolated yield of the desired product.

In Examples 1-6, the chlorination reaction of the compound of formula (II) with NCS was performed in different polar aprotic solvents (Ex. 1: MeCN; Ex. 2: CHCl3; and Ex. 3: IBN) or mixtures of polar aprotic solvents with apolar aprotic solvents (Ex. 4: DMF/toluene; Ex. 5: IBN/MCB; and Ex. 6: MeCN/MCB). Water was removed from the reaction mixtures as much as possible to allow the reactions to be carried out in a substantially water-free environment. Yields ranging from 79% to 95% have been obtained in these reactions. A summary of all experiments is given in Table 1.

In Examples 7-10, the chlorination reactions of the compound of formula (II) with NCS were performed in the presence of water. The addition of water resulted in strongly exothermic reactions and stalling of the chlorination reaction at partial conversion. Examples 8-10 show that practically full conversion of the compound of formula (II) to the compound of formula (I) can be achieved only if an excess of NCS is used. For these experiments, 1.5 g (Ex. 7 and 8), 3.0 g (Ex. 9) and 4.5 g (Ex. 10) of water were added. Overall, one can see that an increase in the amount of water leads to a higher excess of NCS needed to achieve a high conversion of the compound of formula (II) to the compound of formula (I). Additionally, and not less importantly, the amount of the compound of formula (I) obtained in these reactions decreases with increasing amount of overall water in the reaction mixture. This data is summarized in Table 1.

TABLE 1

Summary of examples 1-10

| Exp. Nr. | Solvent | Water min.,* [g] | Rct. mix., [g] | Compound [II], [g] | NCS, [g] | Water rel. to rct. mix., [wt. %] | Water rel. to compound [II], [wt. %] | Water rel. to NCS, [wt. %] | NCS rel. to compound [II], [molar equiv.] | NCS rel. to compound [II], [weight equiv.] | Yield compound [I], [%] |
|---|---|---|---|---|---|---|---|---|---|---|---|
| 1 | MeCN | 0.136 | 451.4 | 92.8 | 58.6 | 0.03 | 0.15 | 0.23 | 1.07 | 0.631 | 91 |
| 2 | HCCl3 | 0.048 | 501.4 | 92.8 | 58.6 | 0.01 | 0.05 | 0.08 | 1.07 | 0.631 | 89 |
| 3 | IBN | 0.221 | 756.0 | 92.8 | 63.2 | 0.03 | 0.24 | 0.35 | 1.16 | 0.681 | 85 |
| 4 | DMF/tol | 1.338 | 467.9 | 92.8 | 75.1 | 0.29 | 1.44 | 1.78 | 1.37 | 0.809 | 79 |
| 5 | IBN/MCB | 0.295 | 449.0 | 90.0 | 59.0 | 0.07 | 0.33 | 0.50 | 1.07 | 0.656 | 86 |
| 6 | MeCN/MCB | 7.030 | 20915.0 | 4600.0 | 2915.0 | 0.03 | 0.15 | 0.24 | 1.04 | 0.634 | 95 |
| 7 | MeCN with water (no add. feeding) | 4.449 | 452.9 | 92.8 | 58.6 | 0.98 | 4.79 | 7.59 | 1.07 | 0.631 | 30 |
| 8 | MeCN with water (with add. feeding) | 5.697 | 478.9 | 92.8 | 84.6 | 1.19 | 6.14 | 6.73 | 1.55 | 0.912 | 79 |
| 9 | MeCN with water (with add. feeding) | 8.565 | 508.9 | 92.8 | 113.1 | 1.68 | 9.23 | 7.57 | 2.07 | 1.219 | 40 |
| 10 | MeCN with water (with add. feeding) | 10.262 | 514.5 | 92.8 | 117.2 | 1.99 | 11.06 | 8.76 | 2.14 | 1.263 | 49 |

*assuming: 0.00 wt. % water in NCS solvent mixture after drying, and 0.05 wt % water in compound [II] after drying unless noted differently

What is claimed:

1. An improved process for preparing a compound of formula (I)

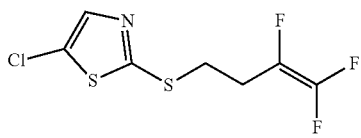

which comprises reacting a compound of formula (II)

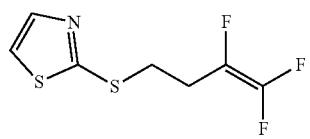

with N-chlorosuccinimde (NCS) in the presence of water, the improvement comprising (i) performing the step of reacting the compound of formula (II) with NCS in the presence of a reduced amount of water, and/or (ii) performing the step of reacting the compound of formula (II) with excess molar amount of NCS.

2. The improved process of claim 1, wherein the improvement comprises performing the step of reacting the compound of formula (II) with NCS in the presence of a reduced amount of water, and wherein:
   a. the reduced amount of water is a concentration of water between 0 wt. % and 5 wt. % relative to the total weight of the reaction mixture,
   b. the reduced amount of water is a concentration of water between 0 wt. % and 7 wt. % relative to the weight of the compound of formula (II) in the reaction mixture, and/or
   c. the reduced amount of water is a concentration of water between 0 wt. % and 7 wt. % relative to the weight of NCS in the reaction mixture.

3. The improved process of claim 2, wherein:
   a. the molar ratio of NCS to the compound of formula (II) is from about 5:1 to about 1:5, or
   b. the weight ratio of NCS to the compound of formula (II) is from about 3:1 to about 1:8.5.

4. The improved process of claim 1, wherein the improvement comprises performing the step of reacting the compound of formula (II) with NCS using an excess molar amount of NCS, and wherein:
   a. the molar ratio of NCS to the compound of formula (II) is from about 5:1 to about 1.01:1, or
   b. the weight ratio of NCS to the compound of formula (II) is from about 3:1 to about 0.6:1.

5. The improved process of claim 1, wherein:
   a. the reaction mixture has a water content of less than 1 wt. % relative to the weight of NCS in the reaction mixture, and the weight ratio of NCS to the compound of formula (II) is from about 0.6:1 to about 0.7:1,
   b. the reaction mixture has a water content of less than 1 wt. % relative to the weight of the compound of formula (II) in the reaction mixture, and the weight ratio of NCS to the compound of formula (II) is from about 0.6:1 to about 0.7:1,
   c. the reaction mixture has a water content of less than 1 wt. % relative to the weight of NCS in the reaction mixture, and the molar ratio of NCS to the compound of formula (II) is from about 1:1 to about 1.2:1,
   d. the reaction mixture has a water content of less than 1 wt. % relative to the weight of the compound of formula (II) in the reaction mixture, and the molar ratio of NCS to the compound of formula (II) is from about 1:1 to about 1.2:1,
   e. the reaction mixture has a water content of between 1 wt. % to 7 wt. % relative to the weight of NCS in the reaction mixture, and the weight ratio of NCS to the compound of formula (II) is from about 0.7:1 to about 1:1,
   f. the reaction mixture has a water content of between 1 wt. % to 7 wt. % relative to the weight of the compound of formula (II) in the reaction mixture, and the weight ratio of NCS to the compound of formula (II) is from about 0.7:1 to about 1:1,
   g. the reaction mixture has a water content of between 1 wt. % to 7 wt. % relative to the weight of NCS in the reaction mixture, and the molar ratio of NCS to the compound of formula (II) is from about 1.2:1 to about 1.7:1, or
   h. the reaction mixture has a water content of between 1 wt. % to 7 wt. % relative to the weight of the compound of formula (II) in the reaction mixture, and the molar ratio of NCS to the compound of formula (II) is from about 1.2:1 to about 1.7:1.

6. The improved process of claim 1, wherein:
   a. the reduced amount of water in the reaction mixture is achieved by drying the compound of formula (II) prior to performing the reacting step,
   b. the reduced amount of water in the reaction mixture is achieved by drying the NCS prior to performing the reacting step, and/or
   c. the reduced amount of water in the reaction mixture is achieved by selecting a batch of NCS with low water content.

7. The improved process of claim 1, wherein the reaction mixture comprises at least one solvent and wherein:
   a) the reduced amount of water is achieved by drying the solvent prior to using it in the reaction mixture,
   b) the reduced amount of water is achieved by selecting a low water content solvent, and/or
   c) the reduced amount of water is achieved by selecting a batch of solvent with low water content.

8. The improved process of claim 7, wherein:
   a. the NCS is dissolved in the solvent to form a solution prior to performing the reaction step and the improvement comprises drying the solution prior to performing the reaction step, or
   b. the NCS is suspended in the solvent to form a suspension prior to performing the reaction step and the improvement comprises drying the suspension prior to performing the reaction step.

9. The improved process of claim 8, wherein the dried solution or suspension has a water content from 0 wt. % to 2 wt. % relative to the total weight of the solution or suspension.

10. The improved process of claim 7, wherein:
    a. one of the at least one solvent is a polar solvent selected from nitriles, amides, ethers, nitro-groups containing solvents, chlorinated solvents and combinations thereof, and/or b. one of the at least one solvent is a non-polar solvent selected from aliphatic hydrocarbons, aromatic hydrocarbons, chlorinated hydrocarbon and combinations thereof.

11. The improved process of claim 7, wherein the solvents have a dielectric constant of about ε=2-40.

12. The improved process of claim 7, wherein the improved process further comprises the step of:
   (a) removing succinimide from the reaction mixture followed by removing the solvent from the reaction mixture to obtain the compound (I); or
   (b) removing the solvent from the reaction mixture followed by removing succinimide from the reaction mixture to obtain the compound (I).

13. The improved process of claim 12, wherein the improved process further comprises a step of recovering NCS comprising adding to the removed succinimide a buffer, an acid or a base, and a chlorinating agent, wherein the step is performed at a temperature of less than about 50° C.

14. A process of preparing a compound of formula (I)

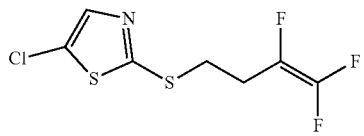
(I)

comprising reacting a compound of formula (II)

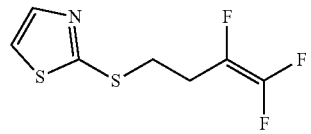
(II)

with N-chlorosuccinimide (NCS) in a low water content reaction mixture, wherein the process comprises (i) obtaining a low water content compound of formula (II), and/or (ii) obtaining a low water content NCS.

15. The process of claim 14, wherein:
a. the obtained compound of formula (II) has a water content from 0 wt. % to 0.2 wt. %, and/or
b. the obtained compound of NCS has a water content from 0 wt. % to 2 wt. %.

16. A process for preparing a compound of formula (III)

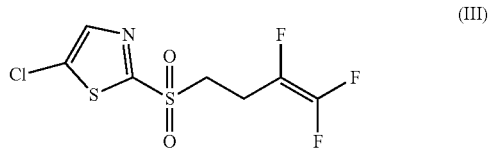 [SMILES: O=S(=O)(CCC(F)=C(F)F)c1ncc(Cl)s1]
(III)

comprising converting the compound of formula (I) prepared according to the process of claim 1.

17. A method of increasing yield of a compound of formula (I) in a process of synthesizing the compound of formula (I) which involves reacting a compound of formula (II) with NCS in the presence of water, wherein the method comprises (i) performing the step of reacting the compound of formula (II) with NCS in the presence of less water so as to increase the yield of the compound of formula (I) relative to a process where more water is present during the reacting step, or (ii) adding excess molar amount of NCS to the reaction mixture.

18. The method of claim 17, wherein the method comprises:
a. drying the compound of formula (II) prior to performing the reacting step,
b. dissolving the compound of formula (II) in a solvent to form a solution and drying the solution prior to performing the reacting step,
c. drying the NCS prior to performing the reacting step,
d. dissolving or suspending the NCS in a solvent to form a solution or suspension and drying the solution or suspension prior to performing the reacting step,
e. selecting a low water content batch of NCS,
f. selecting a low water content solvent,
g. selecting a batch of solvent with low water content, and/or
h. drying the reaction equipment prior to use.

19. The improved process of claim 1, wherein the improvement comprises performing the step of reacting the compound of formula (II) with NCS in the presence of a reduced amount of water, and wherein the reduced amount of water is a concentration of water less than or equal to 2wt. % relative to the total weight of the reaction mixture.

20. The improved process of claim 5, wherein the molar ratio of NCS to the compound of formula (II) is from about 2:1 to about 1.01:1.

* * * * *